(12) United States Patent
Scherzinger et al.

(10) Patent No.: US 8,393,200 B2
(45) Date of Patent: Mar. 12, 2013

(54) DEVICE AND METHOD FOR MEASURING MECHANICAL PROPERTIES OF MATERIALS

(75) Inventors: Bernhard Scherzinger, Esslingen (DE); Hans-Peter Vollmar, Stuttgart (DE); Thomas Wolf, Karlsruhe (DE)

(73) Assignee: Helmut Fischer GmbH, Institut fuer Elektronik und Messtechnik, Sindelfingen (DE)

( * ) Notice: Subject to any disclaimer, the term of this patent is extended or adjusted under 35 U.S.C. 154(b) by 612 days.

(21) Appl. No.: 12/592,185

(22) Filed: Nov. 20, 2009

(65) Prior Publication Data

US 2010/0122572 A1 May 20, 2010

(30) Foreign Application Priority Data

Nov. 20, 2008 (DE) .......................... 10 2008 058 369

(51) Int. Cl.
*G01N 3/48* (2006.01)

(52) U.S. Cl. .............................................. 73/81; 73/85
(58) Field of Classification Search ........................ None
See application file for complete search history.

(56) References Cited

U.S. PATENT DOCUMENTS

| 5,869,751 | A  | * | 2/1999  | Bonin ............................... 73/105 |
| 6,142,010 | A  | * | 11/2000 | Merck et al. ....................... 73/81 |
| 6,718,820 | B2 | * | 4/2004  | Kwon et al. ........................ 73/81 |
| 2008/0011119 | A1 | * | 1/2008 | Bartosch .......................... 74/567 |
| 2008/0288763 | A1 | * | 11/2008 | Reik ................................. 713/2 |

FOREIGN PATENT DOCUMENTS

| DE | 103 20 725 A1 | 11/2004 |
| DE | 10 2006 052 153 A1 | 5/2008 |
| DE | 10 2006 052 522 A1 | 5/2008 |

* cited by examiner

*Primary Examiner* — Hezron E Williams
*Assistant Examiner* — Mark A Shabman
(74) *Attorney, Agent, or Firm* — Kreigsman & Kriegsman

(57) ABSTRACT

The invention relates to an apparatus and a method for measuring mechanical properties of materials using an indenter which has a predetermined geometry, a device for generating force permitting the indenter to penetrate into a material sample surface of an object of measurement, and a device for measuring the penetration depth, wherein, arranged between a force application portion on which the device for generating force is applied and a shaft with an indenter tip facing towards the material surface of the object of measurement, the indenter has at least one micro-mechanical motion actuator by which at least one radial deflection of the shaft with respect to the force absorption portion of the indenter is capable of being activated or detected.

17 Claims, 3 Drawing Sheets

DEVICE AND METHOD FOR MEASURING MECHANICAL PROPERTIES OF MATERIALS

Figure 1:
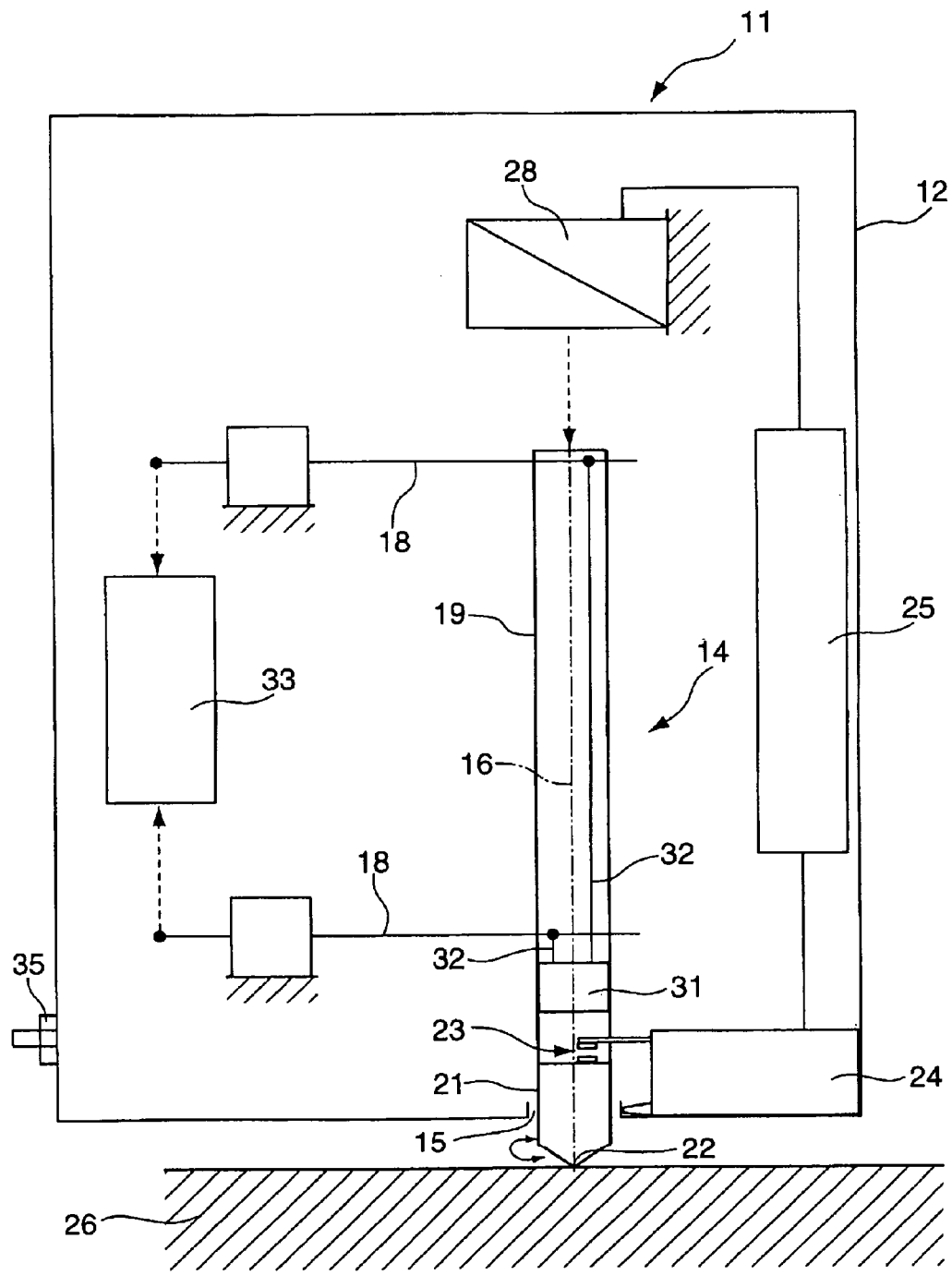

The invention relates to an apparatus and a method for measuring mechanical properties of materials using an indenter with a predetermined geometry a well as a device for generating force permitting the indenter to penetrate into a material sample surface, and a device for measuring the penetration depth.

An apparatus and a method of this type for measuring mechanical properties of materials have been known from DE 10 2006 052 153 A1. In this document, the device for generating force and the device for measuring the penetration depth are designed to be provided in the form of first and second comb-drive actuators, the comb-drive actuator having two comb-shaped electrodes which are each provided with a plurality of comb fingers aligned parallel with each other in such a way that the comb fingers of the two comb-shaped electrodes partially overlap, depending on an electrical voltage applied thereto. This is aimed at enabling an increased resolution of the force generation and an increased resolution of the penetration depth measurement, which, in addition, is insensitive to the different types of sample materials. In this apparatus, a first comb-drive actuator and a lateral comb-drive actuator are provided and aligned in such a manner that a movement of the movable comb finger parallel to its orientation will lead to a movement of the indenter in a direction normal to the material surface. The further comb-drive actuator is provided as a transverse comb-drive actuator and is oriented in such a way that the indenter is displaceable transversely across the material surface. The assembly and configuration of an apparatus of this type is very complex and expensive. At the same time, the lateral comb-drive actuator and the transverse comb-drive actuator may influence each other mutually during the measuring of mechanical properties of materials, which adversely affects the accuracy of measurement.

A micromechanical motion sensor, known from the DE 103 20 725 A1, is capable of detecting a deflection imported to an oscillatably mounted bar spring element exited to a permanent periodic oscillation by an electrostatic oscillating drive to which a periodic drive voltage is applied. Further a rotary rate sensor with two sensitive axes is known from DE 10 2006 052 522 A1, which detects the radial deflection analogous to a micromechanical comb-drive actuator of the DE 103 20 725 A1.

Therefore, it is an object of the present invention to provide an apparatus and a method for measuring mechanical properties of materials which are both simple in terms of layout and structure and permit an improved accuracy of measurement in determining the mechanical properties of materials.

This object is achieved, according to the present invention, by means of an apparatus in which, arranged between a force application portion of the indenter where the device for generating force is applied and a shaft of the indenter, said indenter has at least one micro-mechanical motion actuator by which at least one radial deflection of the shaft with respect to the force absorption portion of the indenter is capable of being activated or detected. This assembly has the advantage that during the penetration, or after the penetration, of the shaft into the material surface the shaft is rotationally drivable by means of the micro-mechanical motion actuator, the force necessary for applying the rotation being detectable, or the accomplished rotation with respect to an initial position being detectable, and the mechanical properties of the material being determinable subsequently through a relation of dependence based on the determined force required for applying the penetration movement of the shaft into the surface of the material. Through the decoupling of the rotational movement or the radial deflection of the shaft with respect to the penetration movement of the indenter normally to the material surface, a mutual impairment of the detected values is minimised or eliminated, thus enabling an improved measurement or detection of the properties of the material.

According to a preferred configuration of the invention, the device for measuring the penetration depth is designed to detect a deflection of the indenter normally to the measurement surface on the shaft of the indenter. Thus it is possible to detect the penetration distance of the shaft in a direct manner which preferably has a constant distance between the distance detection member on the shaft and the indenter tip. This permits an accurate detection of the penetration depth. A detection of the penetration movement on the force application portion of the indenter might be subject to errors due to the interposed micro-mechanical motion actuator.

According to a preferred configuration of the invention, the micro-mechanical motion actuator is realized as a rotationally drivable comb-drive actuator. This makes it possible to maintain small-scale structures so as to realise small-sized indenters. In addition, data acquisition in the micro range or nano-range is made possible.

According to a preferred configuration of the rotationally drivable comb-drive actuator, the latter is designed to be fabricated using a LIGA process or to be realised as a micro-electromechanical system (MEMS). This makes it possible to fabricate actuators with high resolution and accuracy. Furthermore, this enables the values of measurement to be acquired in a simple manner.

The apparatus according to the invention preferably has an indenter that is realised in at least two parts, a rotating joint being provided between the shaft and the force application portion, said joint being realised so as to be rigid in the longitudinal axis of the indenter when under compression and capable of being deflected in a radial direction with respect to said longitudinal axis. This makes it possible, on the one hand, to transmit the forces involved when the shaft is forced into the surface of the material during a process of measurement and, on the other hand, to superpose a rotational driving of the shaft relative to the force application portion.

The rotating joint of the indenter preferably comprises a first connecting member for receiving the shaft and a second connecting member for mounting to the force absorption portion, the first and second connecting members being preferably capable of being disposed in a radially rotatable manner relative to one another while remaining axially at a constant distance from one another by means of one or several circumferentially arranged, resilient coupling links. In this was, it is ensured that the indenter, which is realised in two parts, behaves in fact as if it were a one-piece indenter, thus enabling an accurate measurement of the mechanical properties of the materials.

In addition, between two resilient coupling links of the rotating joint, at least one rotationally drivable comb-drive actuator is provided. Comb fingers which are respectively arranged between two comb-shaped electrodes are realised in a slightly arcuate shape, such that these, when in a rotational movement relative to each other, will remain aligned in a quasi-parallel manner relative to one another, thus allowing a more or less large interleaving movement between the comb-shaped electrodes.

According to a preferred configuration, an air gap is provided between the first and second connecting members of the rotating joint. Thus, a frictionless arrangement between the shaft and the force application portion of the indenter may be provided. Alternatively, at least one low-friction sliding element may be provided between the first and second connecting members. In addition, two end faces of the connecting members which are associated with each other may alternatively be designed to have low-friction surfaces, such that during the application of a penetration force onto the indenter as well as after the penetration of the indenter into the material surface has been accomplished, the shaft is capable of being rotationally driven.

According to a further preferred configuration of the invention, the force application portion of the indenter is designed to be formed of an electrically insulating material. This makes it possible to attach an electric conductor directly to the force application portion in order to supply voltage to the micro-mechanical motion actuator, such that no free power supply cords are provided which might have a detrimental influence on the measuring result.

According to a further advantageous configuration of the invention, the indenter, in particular the force application portion, is designed to be received by at least one spring member and held so as to be capable of being deflected in the mounting direction of the indenter, the at least one spring member being made of an electrically conductive material and thus forming a part of the power supply cord of the micro-mechanical motion actuator. Thus it is possible to reduce the number of component parts and the amount of moving masses. Preferably, at least one leaf spring member is used.

The object of the invention is further achieved by a method for measuring mechanical properties of materials in which during or after the penetration of the indenter into the surface of the material at least one micro-mechanical motion actuator, which is positioned between a force absorption portion and a shaft of the indenter, is activated and initiates at least one radial deflection of the shaft relative to the force absorption portion of the indenter, or detects a radial deflection, or initiates and detects a radial deflection. This permits to acquire additional information about the material properties, preferably as far as a material stress in the elastic range of the material is concerned. Due to the force required for the rotational movement and/or the detection of the angle degrees of the activated rotational movement, together with both the force produced for the penetration of the indenter into the surface of the object of measurement and the one of the detected distance, a determination of the properties of the material is enabled. As compared with a method involving a lateral comb-drive actuator and a transversal comb-drive actuator for measuring the mechanical properties of materials, such a method for measuring mechanical properties has the advantage that the application of forces takes place on a defined surface and under continuous contact with the entire surface of the indenter, and that the design and the technical realisation is simplified while at the same time the moving mass and the disturbance arising therefrom is minimised.

According to a further preferred configuration of the invention, a rotational vibration is designed to be conveyed to the micro-mechanical motion actuator realised in the form of a comb-drive actuator capable of being rotationally driven in order to measure said mechanical properties. Thus, it is possible to detect frequency-selective signals, in particular in the unloading phase, and to evaluate them for determining the properties of the materials.

According to a further preferred configuration of the invention, a continuous force is designed to be applied to the indenter by the device for generating force. In doing so, a superposition of the rotational vibration by the micro-mechanical motion actuator may occur, with this rotational vibration occurring preferably periodically. Alternatively, an aperiodic rotational vibration may be initiated.

According to an alternative configuration of the method, a discontinuous or stepped force is designed to be applied to the indenter by the device for generating force. In the case of such a penetration behaviour, the rotational vibration may equally be initiated periodically or aperiodically and superposed upon the penetration movement.

Furthermore, a rotational vibration, in particular a periodic rotational vibration, may be designed to be activated once the penetration phase of the shaft into the surface of the material has been accomplished. This makes it possible to take into account, to a certain degree, the relaxation behaviour of the material. An aperiodic rotational vibration may equally be enabled.

According to a further advantageous configuration of the method, signals are designed to be detected by the comb-drive actuator and evaluated by an evaluation unit during an unloading phase of the rotational movement of the shaft in the surface of the material, which makes it possible to obtain a highly accurate and a continuous determination of the position of the angle of rotation of the indenter.

Figure 2:
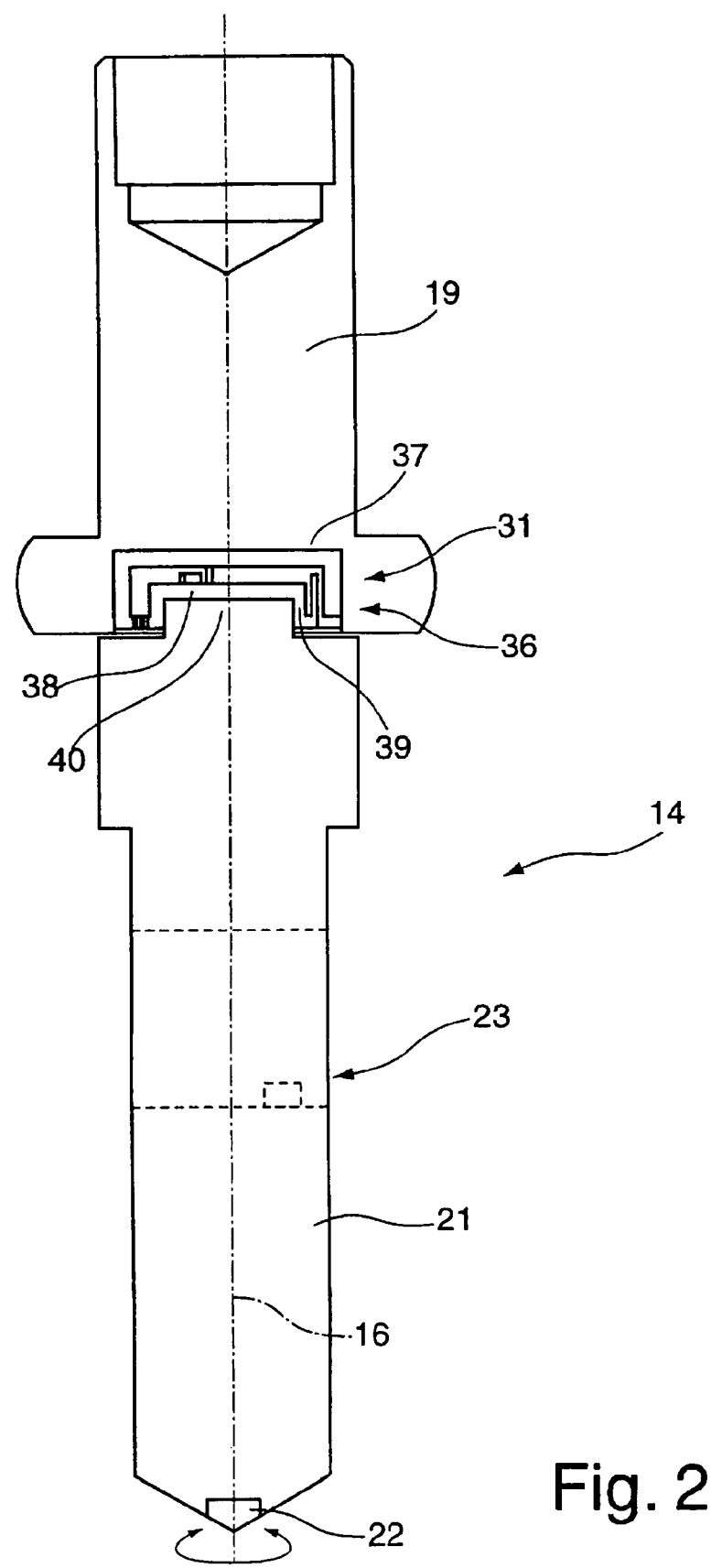
Figure 3:
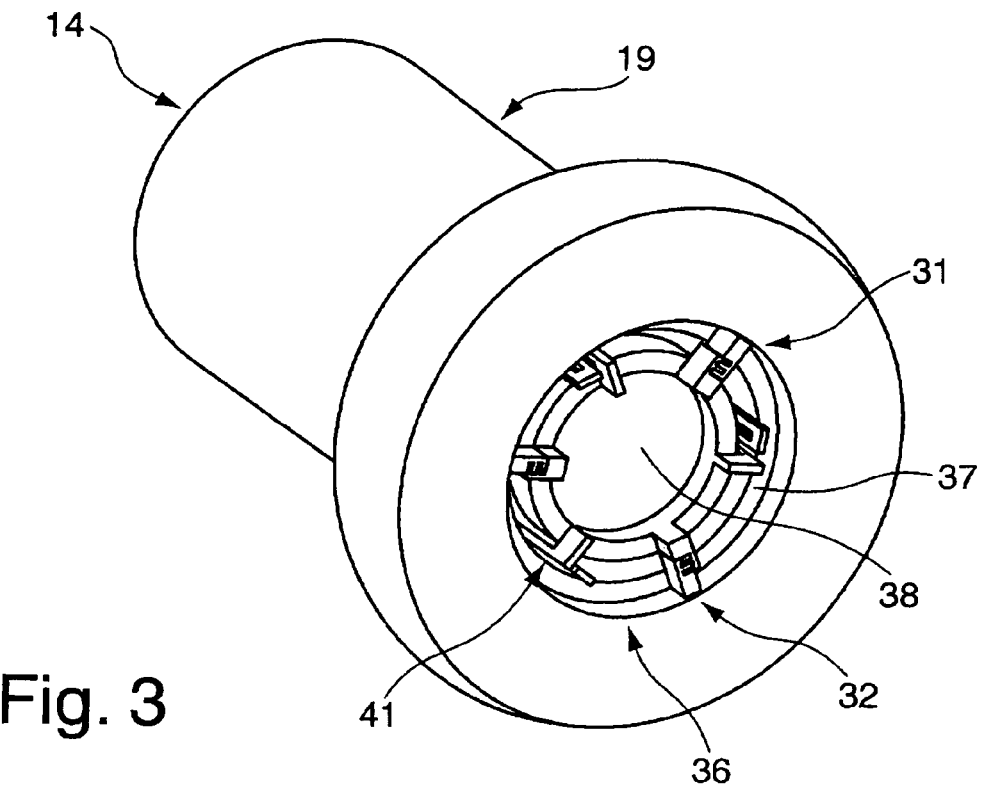
Figure 4:
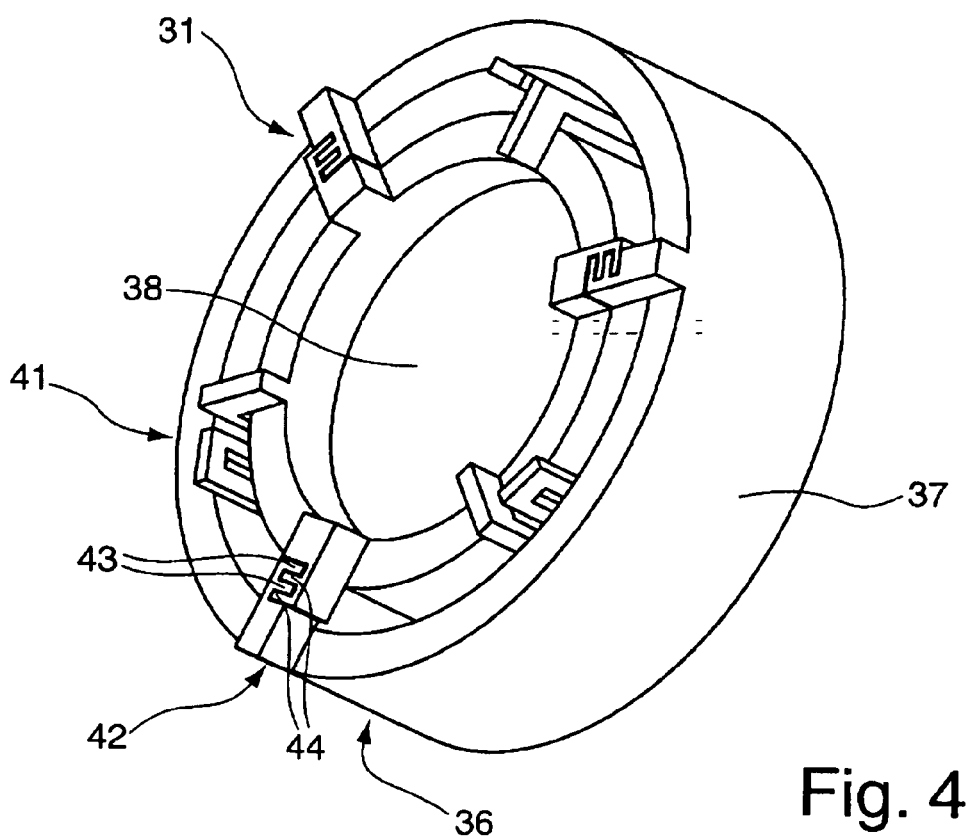

The invention, as well as other advantageous embodiments and developments thereof, will be described and explained in the following with reference being made to the examples shown in the drawings. The characteristics issuing from the description and the drawings may be applied according to the present invention either individually or as a plurality of features taken in any combination. In the drawings:

FIG. 1 is a schematic sectional view of an apparatus according to the invention for measuring mechanical properties of materials, FIG. 2 is a schematic enlarged view of an indenter of the apparatus according to FIG. 1, FIG. 3 is a schematic view of a micro-mechanical motion actuator arranged on the force application portion of the indenter and of a rotating joint, and FIG. 4 is a perspective view of the micro-mechanical motion actuator with a rotating joint.

FIG. 1 schematically represents an apparatus 11 for measuring mechanical properties of materials. The apparatus 11 comprises a box 12 arranged on a holding facility not shown in detail, in particular on a stand. Within the box 12, an indenter 14 is provided which protrudes from a box opening 15 to the outside and is preferably axially guided by this box opening when moving along its longitudinal axis 16. The indenter 14 is received by at least one, preferably two, spring members 18, in particular leaf springs, disposed parallel with each other, said spring members 18 being preferably set in such a way with respect to each other that the indenter 14 is arranged in a quasi zero-force, floating condition when in a starting position or non-deflected position. The indenter 14 is realised in at least two parts and has a force application portion 19 and a shaft 21. The two spring members 18 are applied to the force application portion 19 which may preferably be realised as a cylindrical body or as a small tube, the spring members 18 shaped in the form of leaf springs being deflectable relative to the longitudinal axis 16 of the indenter 14.

The shaft 21 of the indenter 14 comprises an indenter tip 22 which comprises a specific geometrical configuration, depending on the hardness testing method to be employed. The indenter tip 22 may be of pyramidal shape, in particular when made of diamond, or of spherical shape, in particular when made of hardened steel. Further geometrical configurations of the indenter tip 22 may equally be possible. On the shaft 21 at a distance from the indenter tip 22 and preferably within the box 12, a sensor 23 is provided which is part of a device 24 for measuring the penetration depth. Thus it is possible to detect the actual displacement of the indenter tip 22 or the actual depth of penetration into the material surface of an object of measurement 26. The device 24 for measuring the penetration depth is connected with an electronic control equipment of a hardness measuring system 25. A device 28 for generating force by means of which the indenter 14 is moved towards the sample surface of the object of measurement 26 and by means of which the penetration movement is carried out equally communicates with said electronic control equipment for hardness measurement 25. This device 28 is preferably applied on an end of the indenter 14 opposite the indenter tip 22.

Between the force application portion 19 and the shaft 21 of the indenter 14, a micro-mechanical motion actuator 31 is provided by which the shaft 21 is radially deflectable about the longitudinal axis 16 of the indenter 14. The activation of the micro-mechanical motion actuator 31 is ensured via electrical connection lines 32 which are arranged to extend through the force application portion 19 to the micro-mechanical motion actuator 31. The force application portion 19 is preferably designed to be electrically insulated such that the spring members 18 may be contacted by the electronic control equipment 33 in the box. Extending from the point of application of the spring members 18 on the force application portion 19 to the micro-mechanical motion actuator 31, electrical connection lines 32 are provided which are attached to, or integrated into, the force application portion 19, thus making it possible to reduce the proportional amount of moving masses and to exclude any further disturbing effects. The electronic control equipment 33 serves for activating the micro-mechanical motion actuator 31 and is in communication with the electronic equipment of the hardness measuring system 25 and/or of the device 28 for generating force. The apparatus 11 is energized via an electrical connector 35 which is symbolically represented. In addition, further connectors or interfaces for connecting evaluation units and/or computers for controlling the apparatus and for retrieving data and/or signals may be provided.

FIG. 2 represents a schematically enlarged view of the indenter 14. The force application portion 19 is directly connected to the shaft 21 via a rotating joint 36, said rotating joint 36 being realised in such a manner as to be rigid in the axial direction, i.e. along the longitudinal axis 16 of the indenter 14 when under compression, and to permit a deflection in the radial direction, in both senses of rotation, preferably to the same extent. The rotating joint 36 has a first connecting member 37 which is, for example, pot-shaped and is inserted into, or attached in, a recess on the force application portion 19. A second connecting member 38 is provided which is associated with the first connecting member 37 and which has a fastening portion 39 for engaging, for example, a neck 40 of the shaft 21 and holding it in a centred manner therein. Alternative geometrical configurations of the connecting members 37, 38 are also possible, as well as an inversion in the arrangement and accommodation of the respective component members of the indenter 14. The micro-mechanical motion actuator 31 is either integrated in the rotating joint 36 or is arranged on the first and second connecting members 37, 38 in order to provide a torsion of the second connecting member 38 relative to the first connecting member 37.

FIGS. 3 and 4 represent schematically enlarged views of the rotating joint 36 with the micro-mechanical motion actuator 31. The first and second connecting members 37, 38 are each connected by a resilient coupling link 41. This resilient coupling link 41 has a meander-shaped, rectangular structure which allows a radial torsion of the second connecting member 38 with respect to the first connecting member 37 while maintaining at a constant width a gap formed in the axial direction between the first connecting member 37 and the second connecting member 38 as the force for the penetration movement of the indenter 14 is applied. Preferably, the individual land portions of the connecting member are formed with square cross-sections. Other geometries and configurations of the coupling links 41 fulfilling the function of the rotating joint are also envisageable.

Advantageously, the micro-mechanical motion actuator 31 is realised as a comb-drive actuator 42. By way of example, three comb-drive actuators 42 are arranged between the coupling links 41, with the coupling links 41 and the comb-drive actuators 42 being preferably arranged so as to be distributed at equal angles from one another about the circumference. The comb-drive actuator 42 has comb fingers 43 arranged between comb-shaped electrodes 44. By activating the comb-drive actuators 42, it may be achieved that the comb fingers 43 are movable as far as their interleaving depth relative to the comb-shaped electrodes 44 is concerned and that, depending on said interleaving depth a voltage is induced that serves for measuring the rotational movement and is accordingly evaluated, together with other parameters of the devices 24, 28 for measuring the penetration depth and the generating force.

The comb-drive actuator 42 may be fabricated by a LIGA process. Of german origin, the acronym "LIGA" stands for the process steps of Lithographie (lithography), Galvanoformung (electroplating), Abformung (moulding), and refers to a procedure based upon a combination of deep X-ray lithography, electroplating, and micromoulding. This makes it possible to obtain microstructures with very small dimensions of down to 0.2 µm and structures of up to 3 mm in an aspect ratio of up to 50 in the material types plastic, metal, and ceramic. In addition, the comb-drive actuator may be realised as a MEMS structure. Both configurations make it possible to realise the indenter as a micro-scale or nano-scale indenter.

The utilization of a comb-drive 42 of this type which applies a rotational movement or a radial deflection of the shaft 21 with respect to the force application portion 19 has the advantage that both the generation of force and/or the measurement of the angle of radial deflection may be carried out with only one sensor, which makes it possible to achieve a small-sized assembly and a reduction of the sources of error for the measurement. Furthermore, the configuration of the invention with an indenter which consists of at least two parts and comprises a micro-mechanical motion actuator has the advantage that it allows both hardness measurement and material testing.

The apparatus according to the invention makes it possible to perform different procedures for measuring and determining, and also for testing, mechanical properties of materials.

By way of example, the micro-mechanical motion actuator 31 may be designed in such a manner that it is not activated until the indenter 14 touches the material surface of the object of measurement 26. As soon as the indenter 14 penetrates into the object of measurement 26, or after the penetration of the indenter 14 into the object of measurement 26 has been accomplished, the micro-mechanical motion actuator 31 is activated, such that in particular a rotational vibration with respect to the force application portion 19 is conveyed to the shaft 21 which thus experiences a radial deflection. The force applied for performing a deflection may be detected. Alternatively, a rotational movement may be initiated and a performed rotational movement may be measured, or both values may be acquired through the measurement. These are acquired and evaluated in an evaluation unit, together with the force used for generating a penetration movement of the indenter. From the measured values thus obtained, it is possible to determine corresponding mechanical properties of the material of which the object of measurement consists.

In an alternative configuration of the method, a rotational vibration is designed to be conveyed to the micro-mechanical motion actuator 31 during or after the penetration of the indenter 14 into the object of measurement 26. Preferably, the reaction is measured and a resulting phase shift during the unloading phase is acquired and evaluated.

Alternatively, a continuously increasing force, generated, for example, by a direct current, may be designed to be superposed in particular upon a periodic rotational movement. Alternatively, it is also possible to generate an aperiodic rotational movement.

In a further alternative embodiment of the invention, a discontinuous, quasi step-like increase in force may be designed to occur instead of the continuously increasing force, in such a manner that at least one radial deflection may be associated with each step of increased force. Depending on the materials to be tested, the method for measuring mechanical properties may be adapted.

The invention claimed is:

1. An apparatus for measuring mechanical properties of materials, having
    an indenter which has a predetermined geometry,
    a device for generating force with which the indenter penetrates into a material sample surface of an object of measurement, and
    a device for measuring the penetration depth,
    wherein
    arranged between a force application portion on which the device for generating force is applied and a shaft with an indenter tip facing towards the material surface of the object of measurement, the indenter has at least one micro-mechanical motion actuator by which at least one radial deflection of the shaft with respect to the force absorption portion of the indenter is capable of being activated or detected.

2. The apparatus of claim 1, wherein the device for measuring the penetration depth of the indenter detects a deflection on the shaft occurring normally to the material surface of the object of measurement.

3. The apparatus of claim 1, wherein the micro-mechanical motion actuator is realized as at least one rotationally drivable comb-drive actuator.

4. The apparatus of claim 3, wherein the rotationally drivable comb-drive actuator is fabricated according to a LIGA process or as a MEMS system.

5. The apparatus according to claim 1, wherein the indenter is realised in at least two parts, and that a rotating joint is provided between the shaft and the force application portion, said joint being realised so as to be rigid in the longitudinal axis of the indenter when under compression and capable of being deflected radially with respect to said longitudinal axis.

6. The apparatus of claim 5, wherein the rotating joint has a first connecting member for receiving the shaft and a second connecting member for accommodating the force absorption portion.

7. The apparatus of claim 6, wherein the first and second connecting members, by means of several circumferentially arranged, resilient coupling links, are capable of being disposed in such a manner as to be rotatable in the radial direction while remaining at a constant distance, or an almost constant distance, from one another in the axial direction.

8. The apparatus of claim 6, wherein between two resilient coupling links there is provided at least one rotationally drivable comb-drive actuator.

9. The apparatus of claim 6, wherein between the first and second connecting members an air gap is formed or at least one low-friction sliding element is provided, or the end faces of the connecting members associated with each other are provided with low-friction surfaces.

10. The apparatus of claim 1, wherein the force application portion of the indenter is formed of an electrically insulating material.

11. The apparatus of claim 1, wherein the indenter is received by at least one spring member and held so as to be capable of being deflected in the mounting direction of the indenter, and that the at least one spring member is realised so as to be electrically conductive, thus forming a part of an electric power supply cord of the micro-mechanical motion actuator.

12. A method for measuring mechanical properties of materials,
    wherein an indenter with a predetermined geometry penetrates into a material sample surface of an object of measurement with a predetermined force of a device for generating force, and
    wherein the penetration depth of the indenter is detected using a device) for measuring the penetration depth in the material surface of the object of measurement,
    wherein
    during or after the penetration of the indenter into the material surface of the object of measurement at least one micro-mechanical motion actuator, which is positioned between a force absorption portion and a shaft of the indenter, is activated, and
    at least one radial deflection of the shaft relative to the force absorption portion of the indenter is initiated or a rotational movement is detected or a rotational movement is initiated and detected.

13. The method of claim 12, wherein for measuring the mechanical properties, a rotational vibration is conveyed to the micro-mechanical motion actuator realised as at least one rotationally drivable comb-drive actuator.

14. The method according to claim 12, wherein a continuous force is applied to the indenter by the device for generating force.

15. The method according to claim 12, wherein a discontinuous or stepped force is applied to the indenter by the device for generating force.

16. The method of claim 12, wherein during an unloading phase of the introduced rotational movement of the shaft applied to the material surface of the object of measurement signals from the shaft are detected by the micro-mechanical motion actuator and are evaluated by an evaluation unit.

17. The method of claim 12, wherein for measuring the mechanical properties, a periodic rotational vibration is conveyed to the micro-mechanical motion actuator realised as at least one rotationally drivable comb-drive actuator.

* * * * *